United States Patent

Scharbert et al.

[11] Patent Number: 5,969,166
[45] Date of Patent: Oct. 19, 1999

[54] EPOXIDES PRODUCED BY THE OXIDATION OF OLEFINS WITH AIR OR OXYGEN

[75] Inventors: Bernd Scharbert, Frankfurt; Gerhard Lobmaier, Gersthofen; Wolfgang Anton Herrmann, Freising, all of Germany

[73] Assignee: Hoechst Aktiengesellschaft, Frankfurt, Germany

[21] Appl. No.: 08/860,261

[22] PCT Filed: Dec. 19, 1995

[86] PCT No.: PCT/EP95/05027

§ 371 Date: Sep. 12, 1997

§ 102(e) Date: Sep. 12, 1997

[87] PCT Pub. No.: WO96/20788

PCT Pub. Date: Jul. 11, 1996

[30] Foreign Application Priority Data

| Dec. 9, 1904 | [DE] | Germany | 44 47 233 |
| Dec. 30, 1994 | [DE] | Germany | 44 47 231 |
| Dec. 30, 1994 | [DE] | Germany | 44 47 232 |
| Sep. 28, 1995 | [DE] | Germany | 195 36 076 |

[51] Int. Cl.⁶ .................................................. C07D 303/00
[52] U.S. Cl. ........................ 549/512; 502/167; 502/200
[58] Field of Search ............................ 549/512; 502/200, 502/167

[56] References Cited

U.S. PATENT DOCUMENTS

| 3,668,227 | 6/1972 | Scharbert et al. | 260/429 |
| 5,364,952 | 11/1994 | Spiess et al. | 556/44 |

FOREIGN PATENT DOCUMENTS

| 0 015 496 | 9/1980 | European Pat. Off. |
| 0 159 619 | 2/1983 | European Pat. Off. |
| 0 534 356 | 3/1993 | European Pat. Off. |
| 31 35 008 | 4/1982 | Germany |
| 159 075 | 2/1983 | Germany |
| 1 119 476 | 9/1968 | United Kingdom |

*Primary Examiner*—Amelia Owens
*Attorney, Agent, or Firm*—Frommer Lawrence & Haug LLP

[57] ABSTRACT

Catalysts for the selective epoxidization of olefins with atmospheric oxygen, processes for their preparation and processes for the preparation of epoxides by oxidation of olefins with air or oxygen.

Compounds of the formula (1) as catalysts for the selective epoxidization of alkenes $$M_xO_y(L)_z \qquad (1)$$

in which
the indices x, y and z have the following meaning:
x is a whole number from 1 to 3, y is a whole number from 1 to 2x+1, y being selected so that the sum of x+z gives a metal oxidation number of +5 (vanadium) or +6 (molybdenum, ruthenium); z is a whole number in the range from 2 to 2x;
M is molybdenum, ruthenium or vanadium and
L is an N, 0 or S donor ligand.

Heterogeneous catalysts for the selective oxidation of olefins in the presence of oxygen, comprising an inorganic or organic support material and compounds of the formula (1), and a process for the selective epoxidization of alkenes of the formula

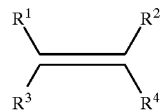

with atmospheric oxygen in the presence of a catalyst of the formula (1) are also described.

12 Claims, No Drawings

EPOXIDES PRODUCED BY THE OXIDATION OF OLEFINS WITH AIR OR OXYGEN

This application is a 371 of PCT/EP95/05027, filed Dec. 19, 1995.

The present invention relates to compounds which selectively catalyze the epoxidation of olefins with atmospheric oxygen, a process for their preparation and a process for the preparation of epoxides by catalytic oxidation of olefins with air or oxygen.

Epoxides (oxiranes), such as, for example, ethylene oxide, propylene oxide, 1,2-butene oxide or similar epoxides, are customary intermediate products for the preparation of a large number of products. The oxirane function in such compounds is very readily reacted, ring-opening reactions taking place with nucleophilic reactants. Epoxides can thus be hydrolyzed, for example, to glycols, which are used as de-icing agents or as reactive monomers for the preparation of condensation polymers.

Polyether polyols prepared by ring-opening polymerization of epoxides are customary as intermediate products for the preparation of polyurethane foams, elastomers, coatings, sealing compositions or similar articles.

The reaction of epoxides with alcohols leads to glycol ethers which are used, for example, as polar solvents.

Many different processes which are said to catalyze the epoxidation of alkenes selectively have been developed for the preparation of epoxides.

Thus, for example, Huybrecht (J. Mol. Catal. 71, 129 (1992); EP-A-311 983) describes the epoxidation of olefins with hydrogen peroxide in the presence of titanium silicate compounds as a catalyst. However, the range of products which is obtained during oxidation of alkenes with titanium silicate catalysts can be controlled only inadequately, so that even minimal changes in the reaction conditions or the reactants employed lead to drastic changes in the proportions of the end products.

The epoxidation of propylene with atmospheric oxygen in the presence of tungsten- or molybdenum-containing catalysts is described in DE-C-22 35 229. The epoxidation reaction is carried out in a solvent which can be oxidized with oxygen to form hydroperoxides. However, in secondary reactions, the hydroperoxides formed lead to oxygen-containing by-products, as a rule alcohols, which are obtained as coupling products of the reaction.

A process for the epoxidation of ethylene with t-butyl hydroperoxide (TBHP) in the presence of molybdenum complexes as the catalyst is described by Kelly et al. (Polyhedron, Volume 5, 271–275 (1986)). Compounds of high catalyst activity which are mentioned are complexes such as, for example, $MoO_2$(8-hydroxyquinoline)$_2$, $MoO_2$ (phenylene-bis-salicylimine) (=$MoO_2$(salphene)), $MoO_2$ (salicylaldoxime)$_2$ and $MoO_2$(5-nitroso-8-hydroxyquinoline)$_2$. The catalyst which is actually active is a molybdenum complex which has already added on TBHP and one equivalent of epoxide.

Although the process proceeds with a high selectivity, an expensive oxidizing agent is used. Problems furthermore arise in respect of the reproducibility, which prevents industrial use of the process.

It is furthermore known that certain ruthenium complexes are capable of reacting olefins with molecular oxygen to give the corresponding epoxide.

The ruthenium complex trans-$(Ru(VI)(L)O_2)^{2+}$ where the ligand L=N,N-(dimethyl-N, N-)bis(2-pyridylmethyl) propylenediamine thus epoxidizes olefins, but only stoichiometrically. Norbornene is converted into 2,3-epoxynorbornane with a yield of 85%. Styrene is epoxidized to the extent of 56% and converted into benzaldehyde with a yield of 39%. On the other hand, cyclohexene is converted into the corresponding ketone without epoxide formation (J.Chem. Soc. Dalton Trans, 1990, 3735).

Conversion of norbornene into the corresponding epoxide is achieved catalytically with the complex cis-dioxo-ruthenium(VI)-bis(dimethyl-phenanthroline)-hexafluorophosphate. After an induction period of 24 hours, 37 catalysis cycles are found after a further 24 hours (J.Chem. Soc. Dalton Trans. 1987, 179).

According to Catal. Org. Reactions (47 (1992), pages 245–248), the two Ru complexes trans-dioxo(5,10,20-tetrakis(2,4,6,trimethylphenyl)[lacuna]-porphyrinato) ruthenium(VI) are capable of epoxidizing alkenes catalytically with oxygen. The first of these complexes is described in U.S. Pat. No. 4,822,899. Norbornene is oxidized with this catalyst with up to 45.6 catalytic cycles within 24 hours. The reactivity of the other olefins employed, such as cylcooctene and 2-methylstyrene, is significantly lower.

The processes described according to the known prior art for epoxidation of alkenes and the catalysts used in these either allow only an inadequate control of the reaction, which means that in addition to the desired epoxide end product, a number of undesirable by-products are also obtained. Furthermore, many of the compounds described do not act catalytically or act only very slowly and in some cases require a very long induction period. It is often necessary to use, in addition to the catalyst employed, an oxidizing agent other than oxygen (generally a hydroperoxide), the reaction product of which must be disposed of after the reaction has been carried out and which furthermore is considerably more expensive than oxygen. Problems also arise in respect of reproducibility, which prevents industrial use of the process.

The oxidation of olefins with air or oxygen as the oxidizing agent would be of great advantage industrially, since the oxidizing agent is available inexpensively and the reaction could proceed without the formation of reduced by-products.

A process for the preparation of epoxides by the catalyzed liquid phase oxidation of olefins with molecular oxygen or air is described in DD-B-159 075. The catalysts employed are epoxidation-active transition metal salts or complexes of molybdenum, for example chlorine, carbonyl or chloronitrosyl complexes, which also contain donor ligands, such as hexamethylphosphoric acid triamide (HMPT), triphenyl phosphite or acetonitrile. The most active compounds here are those which contain HMPT as the donor ligand, HMPT being known as a carcinogenic substance.

The epoxidation of oct-1-ene with molybdenum catalysts was the subject of an investigation in J. Prakt. Chem. (1992, 334, 165–175). The selectivity found for 1,2-epoxyoctane is 34% in the presence of molybdenyl acetylacetonate and 28% in the presence of molybdenum trioxide. It is likewise confirmed that the position of the transition metal in the periodic table and its oxidation state have by far the greatest influence on the catalyst activity, the structure of the catalyst complex itself playing only a minor role.

The best epoxide selectivity to date, of 43.8%, is stated for the complex $MoCl_2(NO)_2(HMPT)_2$ [J. prakt. Chemie, 1984, 326, 1025–1026]. These catalysts all have the disadvantage of leading to epoxide selectivities of only less than 45% (molybdenum (VI) even to selectivities of only ≦35%), and therefore of generating more than 55% of by-products.

The Wissenschaftliche Zeitschrift [scientific journal of TH Leuna-Merseburg] (1985, 27, 282–294), introduces an index for measuring the influence of the catalyst in the liquid phase oxidation of oct-1-ene, being the ratio of the epoxide selectivities obtained from the catalyzed and non-catalyzed reaction. A number greater than 1 describes a catalytic effect. It can be seen from this table that the best value obtained to date is 1.91 for $MoO_2(acac)_2$.

The aim of the present invention is to provide compounds which allow the epoxidation of olefins to be catalyzed selectively and in good yields, only atmospheric oxygen being used as the oxidizing agent. The invention also relates to a process which allows olefins to be oxidized with oxygen or air with high selectivities to give the corresponding epoxides.

It would furthermore be of great advantage if the catalysts used did not have to be employed as unsupported catalysts, i.e. where the expensive metal complex is used in undiluted form in relatively large amounts. Another aim of the invention is therefore to provide catalysts which catalyze the epoxidation of olefins selectively and in good yields, in which the expensive metal proportion is decreased by application to a support material.

The present invention thus relates to compounds of the formula (1)

$$M_xO_y(L)_z \qquad (1)$$

which selectively catalyze the epoxidation of olefins. M is molybdenum, ruthenium or vanadium and L is an N, O or S donor ligand.

The index x is a whole number from 1 to 3, preferably 1 or 2, y is a whole number from 1 to 2x+1, and y is preferably 1 or 2, y being selected so that the sum of x+z gives a metal oxidation level of +5 (vanadium) or +6 (molybdenum, ruthenium). The index z is a whole number in the range from 2 to 2x, and x is preferably 2.

Oxidizing agents which can be employed are hydrogen peroxide or another hydroperoxide, such as, for example, tert-butyl peroxide, or another customary oxidizing agent. In a preferred embodiment, only air or oxygen is used.

The ligand is bonded in bidentate form to the metal center, which can bond up to two such ligands. The dioxo complexes can be present here both as the cis and as the trans isomers. In a preferred embodiment, the vanadium and molybdenum complexes are present as cis isomers and the ruthenium complexes are present as trans isomers.

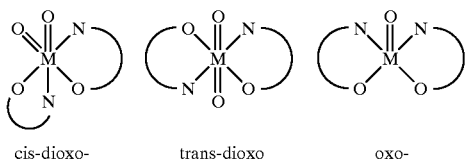

cis-dioxo-    trans-dioxo    oxo-

Donor ligands which are preferably employed are compounds which are derived from the formulae (2), (3) and (4)

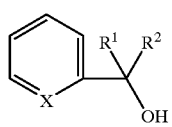

(2)

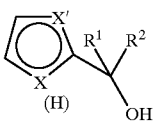

(3)

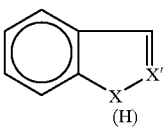

(4)

in which X is N (nitrogen), O (oxygen) or S (sulfur) and X' is N (nitrogen) or C (carbon) and $R^1$ and $R^2$ independently of one another are a branched or unbranched, optionally halogenated $C_1$–$C_{12}$-alkyl radical or an optionally substituted $C_6$–$C_{14}$-aryl or heteroaryl radical, or the two together are a group C=O or C=S. Furthermore, either $R^1$ or $R^2$ can also additionally be a hydrogen radical. The ring can optionally be substituted by alkyl, aryl or alkoxy groups.

In particular, X' in formula (4) is N or C if X is N and X' is C if X is S or O.

Preferred ligands are, for example, 1,1-($C_1$–$C_6$)-alkyl-1-(2-pyridyl)methanol, 1-(2-pyridyl)-cyclohexan-1-ol, 1,1-($C_1$–$C_6$)-perfluoroalkyl-1-(2-pyridyl)methanol, 1,1-($C_1$–$C_6$)-alkyl-1-(2-thiophenyl)methanol, 1,1-($C_1$–$C_6$)-perfluoroalkyl-1-(2-thiophenyl)methanol, 1,1-($C_1$–$C_6$)-alkyl-1-(2-pyrrolyl)methanol, 1,1-($C_1$–$C_6$)-alkyl-1-(2-imidazole)methanol, and 1,1-($C_1$–$C_6$)-perfluoroalkyl-1-(2-imidazole)methanol.

Complexes of formula (1) are prepared by reaction of a suitable precursor with the corresponding ligands in an organic solvent.

Suitable precursors are, for example, the commercially obtainable oxoacetylacetonates, such as molybdenyl acetylacetonate $MoO_2(acac)_2$, or vanadylacetylacetonate $VO(aca-c)_2$. It is furthermore possible to use the oxo-dithiocarbamates, for example molybdenyl bis(N,N-diethyl-dithiocarbamate), the pyridyl and/or acetate complexes of the oxides, the higher oxides, for example molybdenum trioxide, ruthenium oxides or vanadium(V) oxide, or the corresponding acids and salts thereof.

The complex $RuO_2(py)_2(OAc)_2$, which is described in the literature, is preferably used as the starting substance for the preparation of the corresponding ruthenium complexes (Inorg. Chem. 1990, 29, 4190–95). In some cases it may also seem appropriate that the newly prepared complexes are a precursor for other novel complexes.

The precursor is suspended in an organic solvent. Suitable organic solvents are preferably polar protic solvents, such as methanol or ethanol, and aprotic solvents, such as acetonitrile or methyl tert-butyl ether (MTBE).

The corresponding ligand is then added, while stirring. The amount of ligand employed is preferably twice the amount of the precursor employed. The ligand can also be employed in less than or more than the stoichiometric amount, but expensive purification processes are then often necessary. If the precursor employed is soluble, it is generally allowed to dissolve completely before use.

The reaction temperature depends on the solvent used and is in a range from –30° C. up to the boiling point of the solvent, preferably in a temperature range from 0° C. to 25° C. The duration of the reaction is as a rule 2 to 300, preferably 3 to 90 minutes.

After the end of the reaction, the solvent is stripped off in vacuo. If the corresponding complex precipitates out, it is filtered off and washed with the solvent used. If the complex formed remains in solution, this solution is evaporated to dryness and the residue is recrystallized from the solvent used and a non-polar solvent, such as, for example, an n-alkane or diethyl ether. The complexes purified in this way are then dried under a high vacuum.

The compounds according to the invention are capable of epoxidizing olefins selectively in the presence of atmospheric oxygen or another oxidizing agent: they are furthermore suitable generally as oxidation catalysts.

It has furthermore been found, surprisingly, that improved catalyst properties can be achieved if the corresponding molybdenum, vanadium or ruthenium complexes are reacted with organic or inorganic supports.

The present invention therefore also additionally relates to heterogeneous catalysts for the selective oxidation of olefins in the presence of air or oxygen.

Constituents of these catalysts are the compounds of the formula (1) described above.

In addition to the ligands described above, the ligands described in the literature can also be used for the heterogenization of the compounds of the formula (1), such as, for example, for molybdenum of the acetylacetonate complex $MoO_2(acac)_2$ or for ruthenium of $RuO_2(py)_2(OAc)_2$ (Inorg. Chem. 1990, 24, 4190–95).

Suitable support materials are inorganic and organic supports. Examples of inorganic supports are, for example, materials from the following group: aluminum oxide, silicon dioxide, alumosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride and silicon carbide.

Suitable organic supports are all the polymers which offer free donor possibilities, that is to say polymers having O, N or S groups, such as, for example, polypyridine or polyacrylate.

The support material can be added at the start of, during or after the synthesis of the complex of the formula (1), in particular after the synthesis of (1). The starting complex of the formula (1) is here dissolved in an organic solvent or water, the support material is added and the entire mixture is stirred. The ratio of the amounts of the support material/complex (1) is preferably in the range from 1:1 to 1:1000, in particular in the range from 1:2 to 1:100.

The reaction temperature depends on the solvent used and is in a range from −30° C. up to the boiling point of the solvent. The duration of the reaction is as a rule 1 minute to 24 hours, preferably 10 minutes to 8 hours.

After the end of the reaction, the solvent is filtered off. The resulting residue on the filter can be employed in this form or after drying in vacuo or after drying at temperatures in the range from 80 to 300° C.

The heterogeneous catalysts according to the invention are capable of epoxidizing olefins selectively with atmospheric oxygen.

Only oxygen is required as the oxidizing agent, and can be employed in a pure form or as atmospheric oxygen or in a form diluted with an inert gas, such as $CO_2$, $N_2$, noble gases or methane.

The invention furthermore relates to a process for the selective epoxidation of alkenes of the formula

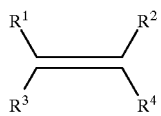

with atmospheric oxygen in the presence of a catalyst. The catalysts used are compounds of the formula (1)

$$M_xO_y(L)_z \qquad (1)$$

The symbols $R_1$, $R^2$, $R^3$ and $R^4$ have the following meaning: $R_1$, $R^2$, $R^3$ and $R^4$ independently of one another are hydrogen, $C_1$–$C_{20}$-alkyl, $C_1$–$C_{12}$-alkoxy or $C_6$–$C_{10}$-aryl, or $R_1$ and $R^2$ together form a ring having 5 to 30, preferably 5 to 8 carbon atoms.

The symbols M and L and the indices x, y and z have the abovementioned meaning.

Aliphatic, optionally branched $C_2$–$C_{30}$-olefins and alicyclic $C_5$–$C_{12}$-olefins, preferably linear olefins having 2 to 12 carbon atoms and cyclic olefins having 5 to 12 carbon atoms are epoxidized selectively, in particular, by the process according to the invention for the epoxidation of olefins.

Oxygen, which can be in a pure form or in a form diluted with an inert gas, such as $CO_2$, $N_2$, noble gases or methane, serves as the oxidizing agent.

The oxidizing conditions are chosen such that noticeable oxidation already occurs without addition of the catalyst, the selectivity of the epoxide formation being low in this case.

The temperature at which the epoxidation reaction can be carried out is in the range from 30 to 500° C., and the pressure range can vary from normal pressure to 200 bar and is preferably not more than 100 bar. The temperature/pressure range is generally to be chosen such that neither the temperature nor the pressure assumes extremely high values, since the reaction will be more difficult to handle under these conditions. A temperature range of 30 to 300° C. and a pressure in the range from normal pressure to 30 bar, for example, has thus proved advantageous for the oxidation of $C_6$–$C_{12}$-alkenes, while the epoxidation of alkenes having less than 6 carbon atoms is preferably carried out at lower temperatures in the range from 120 to 230° C. under pressures in the range from 30 to 100 bar. The reaction is carried out such that the oxidation always takes place in the liquid phase.

The epoxidation of octene using the heterogeneous catalysts according to the invention is in general carried out in a temperature range from 30 to 300° C., preferably in the range from 70 to 130° C. In the case of propene, the temperature is preferably in a range from 100 to 500° C., in particular in the range from 125 to 230° C. The pressure should be in the range from 20 to 200 bar, in particular from 35 to 100 bar.

The liquid phase oxidation is carried out either in the pure olefin or in dilution in a solvent which is stable to oxidation, both in the case of the heterogeneous and in the case of the homogeneous catalysts. Possible suitable solvents are, for example, the following groups: halogenated aromatics, such as, for example, chlorobenzene, 1-choro-4-bromobenzene and bromobenzene, halogenated and non-halogenated hydrocarbons, such as, for example, chloroform, chloropropanol, methylene chloride, 1,2-dichloromethane and trichloroethylene, and furthermore alcohols, in particular $C_1$–$C_{12}$ alcohols, such as ethanol, methanol or propanol, as well as higher alcohols, and water.

The oxidation can be carried out continuously or in a batch process. The catalysts can be added in bulk. The catalyst can also be produced in situ during the catalysis, for example from the precursor and ligands and, if a heterogeneous catalyst is used, if appropriate from the corresponding support material. The reaction can furthermore be accelerated by addition of stoichiometric amounts, based on the catalyst, of an activator, such as hydroperoxides, hydrogen peroxides or peracids, and/or by addition of a free radical initiator, such as azobisisobutyronitrile.

In the continuous procedure, the addition of oxygen is metered such that a residence time in the reactor of less than 60 minutes, preferably less than 1 minute, results. In the batch process, oxygen can be taken up until conversion of the alkene is complete, but an uptake of oxygen up to an alkene conversion of <50% is preferred. An uptake of oxygen of >50% leads to an increase in the conversion, but also to a reduction in the selectivity, since further oxidation of the epoxide increases. The reaction product is worked up and purified, for example by distillation. This also applies to the continuous procedure.

The epoxide yields are improved significantly compared with the prior art with the aid of the process according to the invention using catalysts comprising compounds of the formula (1). Thus, for example, epoxide yields of >50% are achieved in the oxidation of oct-1-ene, while the highest yields in the processes known to date were 43.8%. This means that indices for measuring the influence of the catalyst (ratio of epoxide selectivity from the catalyzed and non-catalyzed reaction) of >2 are achieved with the process according to the invention.

The selectivity of the epoxidation reaction of olefins increases to more than 40%, in particular to $\leq 45\%$, in the presence of the homogeneous vanadium and molybdenum transition metal complexes according to the invention, and to $\geq 30\%$ if the ruthenium transition metal complexes according to the invention are used. In particular, olefins can be epoxidized with a selectivity of $\geq 50\%$ using the molybdenum and vanadium catalysts according to the invention, and olefins can be epoxidized with a selectivity of $\geq 35\%$ if the ruthenium catalysts according to the invention are used.

It is furthermore observed that the influence of the catalyst is increased considerably by the heterogenization described for the catalysts. Thus, in the case of $MoO_2(acac)_2$ on polypyridine, the selectivity for 1,2-epoxyoctane increases to 49%, while that in the homogeneous case with pure $MoO_2(acac)_2$ was in the range from 10 to 35%. Similar effects are also observed with the corresponding Ru compounds.

Generally, it can be said that if the heterogeneous ruthenium complexes according to the invention are used in the epoxidation of higher olefins ($\geq C_6$), selectivities of $\geq 35\%$, in particular $\geq 39\%$ can be achieved, and if the heterogeneous molybdenum complexes according to the invention are used, selectivities of even $\geq 45\%$, in particular $\geq 49\%$, are achieved.

The oxygen used as the oxidizing agent in the process according to the invention is available inexpensively and formation of reduced by-products which must be disposed of after the epoxidation reaction is eliminated.

The compounds of the formula (1) according to the invention and catalysts comprising these compounds are particularly suitable for the oxidation of aliphatic, optionally branched $C_2$–$C_{30}$-alkenes and alicyclic $C_5$–$C_{12}$-alkenes, preferably for the oxidation of linear $C_2$–$C_{30}$-alkenes and alicyclic $C_5$–$C_8$-alkenes, particularly preferably for oxidation of $C_2$–$C_{12}$-alkenes. However, epoxides of longer-chain or higher alkenes are also accessible with the aid of the complexes according to the invention. The olefins can also be substituted here by further alkyl or alkoxy or also by aromatic groups.

The invention is explained in more detail with the aid of the following examples.

EXAMPLES

The following ligands were prepared:

Example 1

L1: 1,1-dimethyl-1-(2-pyridyl)methanol

Example 2

L2: 1,1-diethyl-1-(2-pyridyl)methanol

Example 3

L3: 1,1-dipropyl-1-(2-pyridyl)methanol

Example 4

L4: 1,1-diisopropyl-1-(2-pyridyl)methanol

Example 5

L5: 1,1-di-n-butyl-1-(2-pyridyl)methanol

Example 6

L6: 1-(2-pyridyl)-cyclohexan-1-ol

Ligand synthesis for Examples 1–6:

0.12 mol of butyllithium is slowly added dropwise, under argon, to 300 ml of methyl t-butyl ether, which is cooled to −30° C. During this operation, the temperature should not rise above −20° C. 0.13 mol of 2-bromopyridine, dissolved in 75 ml of methyl t-butyl ether, is now slowly added dropwise to the etherial BuLi solution. The red solution characteristic of organolithium compounds is formed as a result. 0.15 mol of the particular carbonyl compound (listed in Table 1), dissolved in 75 ml of methyl t-butyl ether, is now added dropwise to the dark-red clear solution thus prepared. Here also, the temperature should not rise above −20° C. The solution is stirred at −30° C. for 2 hours and then warmed slowly to 0° C., and is subsequently hydrolyzed cautiously with a little distilled water. Thereafter, the solution is warmed to room temperature and extracted by shaking with a little 15% strength hydrochloric acid. The aqueous phase is then neutralized with 15% strength sodium hydroxide solution and extracted with methyl tert-butyl ether.

The ether phase is then evaporated on a rotary evaporator. The desired product remains, and is purified by recrystallization (solid product) or distillation (liquid product).

Table 1: Carbonyl compounds employed in Examples 1–6, yields (calculated) and spectroscopic data Yields and $H^1$-NMR data:

δ values in ppm

L1: acetone, yield: 79%

δ=8.52 (d), 7.68(t), 7.41 (d), 7.18(t), 1.55(s)

L2: 3-pentanone, yield: 88%

δ=8.51 (d), 7.70 (t), 7.50 (d), 7.19 (t), 1.85 (m), 0.70 (t)

L3: 4-heptanone, yield: 87%

δ=8.49 (d), 7.69 (t), 7.28 (d), 7.17 (t), 1.8 (m), 1.4 (m), 0.82 (t)

L4: 2,4-dimethylpentan-3-one, yield: 88%

δ=8.53 (d), 7.66 (t), 7.26 (d), 7.18 (t), 2.30 (hep.) 0.8 (q)

L5: 5-nonanone, yield: 77%

δ=8.50 (d), 7.69 (t), 7.30 (d), 7.16 (t), 1.8 (m), 1.4 (m), 1.2 (m), 0.79 (t)

L6: cyclohexanone, yield: 77%

δ=8.49 (d), 7.67 (t), 7.35 (d), 7.18 (t), 2.2 (m), 1.8 (m), 1.3 (m)

The following molybdenum complexes were prepared:

Example 7

$MoO_2(L1)_2$ with L1 from Example 1 (cis-dioxo arrangement), yield: 85%

δ=8.68 (d), 7.78 (t), 7.33 (d), 7.24 (t), 1.8 (d)

cis-dioxo arrangement: IR (KBr) ν (Mo=O) 920 (strong), 905 (strong) $cm^{-1}$

Example 8

$MoO_2(L2)_2$ with L2 from Example 2, yield: 79%

δ=8.74 (d), 7.76 (t), 7.28 (d), 7.23 (t), 2.10 (d), 1.0 (d)

Example 9

$MoO_2(L2)_2$ with L3 from Example 3, yield: 82%

δ=8.70 (d), 7.75 (t), 7.25 (d), 7.24 (t), 2.05 (d), 1.6 (d), 1.0 (d)

Example 10

$MoO_2(L4)_2$ with L4 from Example 4, yield: 75%

δ=8.73 (d), 7.72 (t), 7.27 (d), 7.22 (t), 2.01 (m), 1.25 (m)

Example 11

$MoO_2(L5)_2$ with L5 from Example 5, yield: 82%

δ=8.74 (d), 7.76 (t), 7.26 (d), 7.23 (t), 2.01 (m), 1.65 (m), 1.25 (m), 0.8 (m)

Example 12

$MoO_2(L6)_2$ with L6 from Example 6, yield: 82%

δ=8.71 (d), 7.72 (t), 7.29 (d), 7.24 (t), 2.20 (m), 1.75 (m), 1.55 (m)

Example 13

$MoO_2(L7)_2$ with L7=hydroxymethylthiophene (manufacturer: Aldrich), yield: 73%

δ=7.56 (d), 7.15 (d), 6.63 (t), 5.6 (s)

The molybdenum complexes are prepared as described below:

1.5 g (4.5 mmol) of molybdenum dioxodiacetylacetonate are suspended in 100 ml of dried methanol. The mixture is now stirred for 15 minutes and 9 mmol of the particular ligand are then added. The solution is stirred until it is clear. The methanol is now stripped off at room temperature until the complex starts to precipitate out. The solvent is stripped off almost to dryness and the complex is filtered off and washed with ice-cold methanol.

Example 14

$VO_2(L1)_2$ with L from Example 1

1 g of vanadyl(IV) acetylacetonate is dissolved in 100 ml of dried tetrahydrofuran. 0.85 ml of the ligand from Example 1 is then added. The mixture is now stirred at room temperature for 2 hours and the solvent is then stripped off. The complex which has precipitated out is now washed with ice-cold methyl tert-butyl ether (MTBE) and the wash solution is removed with a glass filter. The complex is then dried under a high vacuum.

Yield: 65%

δ=8.68 (d), 7.71 (t), 7.20 (d), 7.15 (dd), 1.9 (d)

Example 15

$RuO_2(Pic)_2$ where Pic=pyridine-2-carboxylic acid (manufacturer: Riedel de Haen)

1 g of the complex $RuO_2(Ac)_2(Py)_2$, in which Ac=acetate and Py=pyridine, is placed under argon and suspended in 100 ml of dried acetonitrile. A dark brown solution with a sediment results. 600 mg of picolinic acid are then added. After 2 minutes, an ocher-colored precipitate separates out, the solution is removed with a cannula and the precipitate is filtered off with suction using a glass frit and washed with ice-cold methanol. The precipitate is now dried under a high vacuum for 12 v hours.

Yield: 225 mg (22%);

$^1$H-NMR (CDCl$_3$) δ=7.58 (d), 7.98 (t), 8.28 (t), 8.61 (d) ppm.

Example 16

$RuO_2(L1)_2$ with 1,1-dimethyl-1-(2-pyridyl)methanol as L1

1 g of the complex $RuO_2(Ac)_2(Py)_2$ is placed under argon and suspended in 100 ml of dried acetonitrile. A dark-brown solution with a sediment results. The mixture is then cooled to −15° C. and 0.550 ml of the ligand is added. The mixture is now stirred for 1 hour and the solvent is stripped off at −15° C. The complex is purified by washing it with ice-cold acetonitrile and the wash solution is removed with a cannula using a glass filter. The complex is then dried under a high vacuum.

Yield: 233 mg (24%);

$^1$H-NMR (CDCl$_3$) δ=1.58 (s), 7.62 (dd), 7.82 (d), 8.21 (t), 9.21 (d)

Comparison Example 1: Autoxidation of oct-1-ene 2.0 ml (12.6 mmol) of oct-1-ene are introduced into a 10 ml reactor temperature-controlled at 100° C. The apparatus is purged with $O_2$ and filled with a pure $O_2$ atmosphere (1 bar). After 6 hours, the uptake of $O_2$ is 10 ml (0.45 mmol). The apparatus is then cooled, exactly 50 μl of heptane (external GC standard) are added to 1 ml of the reaction solution and the solution is analyzed by gas chromatography. The selectivity for 1,2-epoxyoctane is 21%.

Comparison Example 2: Oxidation of oct-1-ene, catalyst: $MoO_2(acac)_2$ 2.0 ml (12.6 mmol) of oct-1-ene and 54 mg of $MoO_2(acac)_2$ (120 μmol) are introduced into a 10 ml reactor temperature-controlled at 100° C. The apparatus is purged with $O_2$ and filled with a pure $O_2$ atmosphere (1 bar). After 150 minutes and an uptake of $O_2$ of 10 ml, the reaction is interrupted by cooling, exactly 50 μl of heptane (external; GC standard). are added to 1 ml of the reaction solution and the solution is analyzed by gas chromatography.

Selectivity for 1,2-epoxyoctane: 7%

Catalyst index: 0.30

The catalyst index is defined as the ratio of the selectivity for epoxide of the catalyzed reaction from this example to the non-catalyzed reaction from Comparison Example 1.

Example 17

Oxidation of octen-1-ene, catalyst $RuO_2(pic)_2$ 2.0 ml (12.6 mmol) of oct-1-ene and 120 μmol of $RuO_2$(pic)$_2$ are introduced into a 10 ml reactor temperature-controlled at 100° C. The apparatus is purged with $O_2$ and filled with an $O_2$ atmosphere (1 bar). After an uptake of $O_2$ of 10 ml within 265 minutes, the reaction is interrupted by cooling, 50 μl of heptane (external GC standard) are added to 1 ml of the reaction solution and a selectivity for 1,2-epoxyoctane of 32% is analyzed by gas chromatography.

Example 18

Oxidation of oct-1-ene, catalyst $RuO_2(L1)_2$ 2.0 ml (12.6 mmol) of oct-1-ene and 120 μmol of $RuO_2$(L1)$_2$ are introduced into a 10 ml reactor temperature-controlled at 100° C. The apparatus is purged with $O_2$ and filled with an $O_2$ atmosphere (1 bar). After an uptake of $O_2$ of 10 ml within 220 minutes, the reaction is interrupted by cooling, 50 μl of heptane (external GC standard) are added to 1 ml of the reaction solution and a selectivity for 1,2-epoxyoctane of 36% is analyzed by gas chromatography.

Example 19

Oxidation of propene, catalyst $RuO_2(L1)_2$ 18 mg of $RuO_2(L1)_2$ are dissolved in 20 ml of chlorobenzene in a 200 ml autoclave and 25 g of propene are condensed at −20° C. The reaction mixture is brought to 150° C., 15 bar of air are forced in at this temperature and the mixture is stirred for 10 minutes. Thereafter, the reaction is interrupted and a gas sample and a liquid sample are taken at 20° C. and are both analyzed by gas chromatography. The selectivity for propene oxide is 15% at an $O_2$ conversion of 55%.

Examples 20–32

Oxidation of oct-1-ene (Table 1):

2.0 ml (12.6 mmol) of oct-1-ene and in each case 120 μmol of the catalyst are introduced into a 10 ml reactor temperature-controlled at 100° C. The apparatus is purged with $O_2$ and filled with a pure $O_2$ atmosphere (1 bar). The time taken for an uptake of $O_2$ of 10 ml is measured, the reaction is interrupted by cooling, exactly 50 μl of heptane (external GC standard) are added to 1 ml of the reaction solution and the solution is analyzed by gas chromatography. In Table 1, the catalysts employed are assigned to the examples and the time taken for the uptake of 10 ml of $O_2$, the epoxide selectivity and the index catalyst index, as defined in Comparison Example 2, are listed.

Example 33

Oxidation of oct-1-ene, more prolonged uptake of $O_2$:

2.0 ml (12.6 mmol) of oct-1-ene and 45 mg of $MoO_2(L2)_2$ (120 μmol) are introduced into a 10 ml reactor temperature-controlled at 100° C. The apparatus is purged with $O_2$ and filled with a pure $O_2$ atmosphere (1 bar). After 360 minutes and an uptake of $O_2$ of 35 ml, the reaction is interrupted by cooling, exactly 50 μl of heptane (external GC standard) are added to 1 ml of the reaction solution and the solution is analyzed by gas chromatography.

Selectivity for 1,2-epoxyoctane: 55%

Catalyst index: 2.63

With the aid of this example, it can be seen that the epoxide selectivity is independent of the conversion (uptake of oxygen; cf. Example 21).

Example 34

Oxidation of oct-1-ene, activation with tert-butyl hydroperoxide:

2.0 ml (12.6 mmol) of oct1-ene, 45 mg of $MoO_2(L2)_2$ (120 μmol) and 10 ml (105 mmol) of a 70% strength tert-butyl hydroperoxide solution in water are introduced into a 10 ml reactor temperature-controlled at 100° C. The apparatus is purged with $O_2$ and filled with a pure $O_2$ atmosphere (1 bar). After 120 minutes and an uptake of $O_2$ of 10 ml, the reaction is interrupted by cooling, exactly 50 μl of heptane (external GC standard) are added to 1 ml of the reaction solution and the solution is analyzed by gas chromatography.

Selectivity for 1,2-epoxyoctane: 53%

Catalyst index: 2.53

It thus becomes clear that the reaction can be accelerated by addition of approximately stoichiometric amounts (based on the catalyst) of hydroperoxide (cf. Example 21).

Example 35

Oxidation of propene:

18 mg of $MoO_2(L1)_2$ are dissolved in 20 ml of chlorobenzene in a 200 ml autoclave and 15 g of propene are condensed in at −20° C. The reaction mixture is brought to 180° C., 15 bar of air are forced in at this temperature and the mixture is stirred for 10 minutes. The reaction is then interrupted by cooling and a gas sample and a liquid sample are taken at 20° C. and are both analyzed by gas chromatography. The selectivity for propene oxide is 21% at an $O_2$ conversion of 85%.

TABLE 1

| Example | Formula | Ligand | Synthesis | Time/ uptake of 10 ml of $O_2$ | Epoxide selectivity | Catalyst index |
|---|---|---|---|---|---|---|
| 20 | $MoO_2(L1)_2$ | 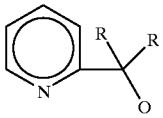 | | 200 min | 51% | 2.42 |

R = $CH_3$

TABLE 1-continued

| Example | Formula | Ligand | Synthesis | Time/ uptake of 10 ml of $O_2$ | Epoxide selectivity | Catalyst index |
|---|---|---|---|---|---|---|
| 21 | $MoO_2(L2)_2$ | pyridine with R,R,O substituent; R = CH₂—CH₃ | | 210 min | 54% | 2.58 |
| 22 | $MoO_2(L3)_2$ | pyridine with R,R,O substituent; R = n-propyl | | 200 min | 52% | 2.47 |
| 23 | $MoO_2(L4)_2$ | pyridine with R,R,O substituent; R = iso-propyl | | 210 min | 50% | 2.38 |
| 24 | $MoO_2(L5)_2$ | pyridine with R,R,O substituent; R = n-butyl | | 215 min | 46% | 2.20 |
| 25 | $MoO_2(L6)_2$ | pyridine with cyclohexyl-O substituent | | 190 min | 48% | 2.29 |
| 26 | $MoO_2(L7)_2$ | thiophene with H,N,O substituent | | 170 min | 50% | 2.38 |
| 27 | $MoO_2(L8)_2$ | pyridine with H,N,O substituent | Polyhedron 5 (1986) 271 | 360 min | 45% | 2.14 |
| 28 | $MoO_2(L9)_2$ | pyridine with R,R,N,O substituent | J. Am. Soc. 115 (1993), 2714 | 150 min | 45% | 2.14 |

TABLE 1-continued

| Example | Formula | Ligand | Synthesis | Time/ uptake of 10 ml of $O_2$ | Epoxide selectivity | Catalyst index |
|---|---|---|---|---|---|---|
| 29 | $MoO_2(L10)_2$ | 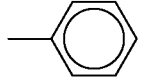 | as 11 | 135 min | 41% | 1.95 |
| 30 | $RuO_2(L1)_2$ | 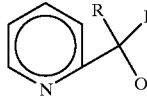<br>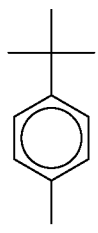 | | 265 min | 32% | 1.52 |
| 31 | $RuO_2(L1)_2$ | as 20 | | 220 min | 36% | 1.71 |
| 32 | $VO(L1)_2$ | as 20 | | 190 min | 42% | 2.00 |

Example 36

Reaction of $MoO_2(acac)_2$ with polypyridine RReillex 402

200 mg of $MoO_2(acac)_2$ and 900 mg of polypyridine RReillex 402 are stirred in 30 ml of acetonitrile at 25° C. for 4 hours. The reaction mixture is then filtered and the residue is washed with methylene chloride and dried in vacuo. 930 mg of a beige material, which is employed as a catalyst in this form, are obtained.

Example 37

Reaction of $RuO_2(OAc)_2(Py)_2$ with polypyridine RReillex 402

250 mg of $RuO_2(OAc)_2(Py)_2$ [prepared in accordance with Inorg. Chem. 1990, 29, 4190–95] and 1.8 g of polypyridine RReillex 402 are stirred in 30 ml of acetonitrile at 25° C. for 4 hours. Thereafter, the reaction mixture is filtered and the residue is washed with methylene chloride and dried in vacuo. 2.0 g of a green material, which is employed as a catalyst in this form, are obtained.

Example 38

Reaction of $RuO_2(OAc)_2(Py)_2$ with aluminum oxide 2.5 g of $RuO_2(OAc)_2(Py)_2$ [prepared in accordance with Inorg. Chem. 1990, 29, 4190–95] are dissolved in 30 ml of acetonitrile, and 9 g of a commercially obtainable aluminum oxide having a typical surface area of 20–40 m²/g are added. This mixture is stirred at room temperature for 4 hours. Thereafter, the solid is filtered off with suction and washed with methylene chloride and the residue on the frit is dried in vacuo. 10.2 9 of a pale-brown material, which is employed as a catalyst in this form, are obtained.

Example 39

Reaction of $RuO_2(OAc)_2(Py)_2$ with silicon dioxide 2.5 g of $RuO_2(OAc)_2(Py)_2$ [prepared in accordance with Inorg. Chem. 1990, 29, 4190–95] are dissolved in 30 ml of acetonitrile, and 9 g of Kieselguhr are added. This mixture is stirred at room temperature for 4 hours. Thereafter, the solid is filtered off with suction and washed with methylene chloride and the residue on the frit is dried in vacuo. 9.8 g of a pale-brown material, which is employed as a catalyst in this form, are obtained.

Example 40

Oxidation of oct-1-ene, catalyst from Example 36

2.0 ml (12.6 mmol) of oct-1-ene and 200 mg of the catalyst material from Example 1 are introduced into a 10 ml reactor (septum, reflux condenser-gas buret) temperature-controlled at 100° C. The apparatus is purged with $O_2$ and filled with a pure $O_2$ atmosphere (1 bar). After 190 minutes and an uptake of $O_2$ of 10 ml, the reaction is interrupted by cooling, exactly 50 µl of heptane (external GC standard) are added to 1 ml of the reaction solution and a selectivity for 1,2-epoxyoctane of 49% is analyzed by gas chromatography.

Example 41

Oxidation of oct-1-ene, catalyst from Example 37

2.0 ml (12.6 mmol) of oct-1-ene and 200 mg of the catalyst material from Example 2 are introduced into a 10 ml reactor (septum, reflux condenser-gas buret) temperature-controlled at 100° C. The apparatus is purged with $O_2$ and filled with a pure $O_2$ atmosphere (1 bar). After 190 minutes and an uptake of $O_2$ of 10 ml, the reaction is interrupted by cooling, exactly 50 µl of heptane (external GC standard) are added to 1 ml of the reaction solution and a selectivity for 1,2-epoxyoctane of 45% is analyzed by gas chromatography.

Example 42

Oxidation of oct-1-ene, catalyst from Example 38

2.0 ml (12.6 mmol) of oct-1-ene and 200 mg of the catalyst material from Example 3 are introduced into a 10 ml reactor (septum, reflux condenser-gas buret) temperature-controlled at 100° C. The apparatus is purged with $O_2$ and filled with a pure $O_2$ atmosphere (1 bar). After 90 minutes and an uptake of $O_2$ of 10 ml, the reaction is interrupted by cooling, exactly 50 µl of heptane (external GC standard) are added to 1 ml of the reaction solution and a selectivity for 1,2-epoxyoctane of 39% is analyzed by gas chromatography.

Example 43

Oxidation of oct-1-ene, catalyst from Example 39

Exactly 2.0 ml (12.6 mmol) of oct-1-ene and 200 mg of the catalyst material from Example 4 are introduced into a 10 ml reactor (septum, reflux condenser-gas buret) temperature-controlled at 100° C. The apparatus is purged with $O_2$ and filled with a pure $O_2$ atmosphere (1 bar). After 100 minutes and an uptake of $O_2$ of 10 ml, the reaction is interrupted by cooling, exactly 50 µl of heptane (external GC standard) are added to 1 ml of the reaction solution and a selectivity for 1,2-epoxyoctane of 39% is analyzed by gas chromatography.

Example 44

Oxidation of propene, catalyst from Example 39

200 mg of catalyst from Example 4 in 20 ml of chlorobenzene are introduced into a 200 ml autoclave and 25 g of propene are condensed in at −20° C. The reaction mixture is brought to 150° C., 15 bar of air are forced in at this temperature and the mixture is stirred for 10 minutes. Thereafter, the reaction is interrupted by cooling and a gas sample and a liquid sample are taken at 20° C. and are both analyzed by gas chromatography. The selectivity for propene oxide is 25%.

We claim:

1. A compound of the formula (1) as a catalyst for selective epoxidization of alkenes $$M_xO_y(L)_z \quad (1)$$

in which the indices x, y and z have the following meaning:
x is a whole number from 1 to 3, y is a whole number from 1 to 2x+1, y being selected so that the sum of x+z gives a metal oxidation number of +6; z is a whole number in the range from 2 to 2x;

M is ruthenium or molybdenum

L is an N, O or S donor ligand, with the proviso that, in particular in the case where M is Mo, L is a compound which is derived from a compound of the formula (2), (3) or (4),

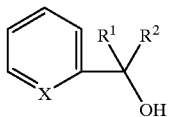

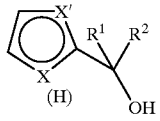

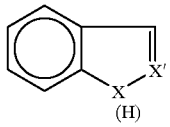

in which

X is N O or S and X' is N or C and $R^1$ and $R^2$ independently of one another are a branched or unbranched, optionally halogenated $C_1$–$C_{12}$-alkyl radical or an optionally substituted $C_6$–$C_{14}$-aryl or heteroaryl radical, or the two together are a group C=O or C=S, or $R^1$ or $R^2$ is a hydrogen radical, and the selectivity in the epoxidization reaction is more than 45% if a molybdenum compound is used and is ≧30% if a ruthenium compound is used.

2. A heterogeneous catalyst for the selective oxidation of olefins in the presence of oxygen, comprising an inorganic or organic support material and a compound of the formula (1)

$$M_xO_y(L)_z \quad (1)$$

in which the indices x, y and z have the following meaning:
x is a whole number from 1 to 3, y is a whole number from 1 to 2x+1, y being selected so that the sum of x+z gives a metal oxidation number of +6; z is a whole number in the range from 2 to 2x;

M is ruthenium or molybdenum

L is an N, O or S donor ligand, with the proviso that, in particular in the case where M is Mo, L is a compound which is derived from a compound of the formula (2), (3) or (4),

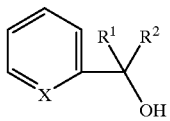

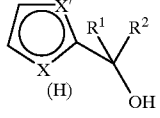

-continued (4)

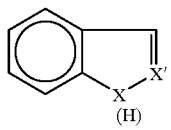

in which

X is N, O or S and X' is N or C and

R$^1$ and R$^2$ independently of one another are a branched or unbranched, optionally halogenated C$_6$–C$_{12}$-alkyl radical or an optionally substituted C$_6$–C$_{14}$-aryl or heteroaryl radical, or the two together are a group C=O or C=S, or R$^1$ or R$^2$ is a hydrogen radical, and the selectivity in the oxidization of olefins is more than 45% if a molybdenum compound is used.

3. A compound as claimed in claim 1, wherein the complex of the formula (1) is readily soluble in organic solvents.

4. A catalyst as claimed in claim 2, wherein the inorganic or organic support material used is a material selected from the group consisting of: aluminum oxides, silicon dioxide, alumosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, silicon nitride or silicon carbide or polypyridines or polyacrylates.

5. A process for the selective epoxidization of alkenes of the formula

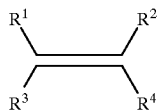

with only atmospheric oxygen as the oxidizing agent in the presence of a catalyst of the formula (1)

$$M_xO_y(L)_z \quad (1)$$

in which the symbols R$^1$, R$^2$, R$^3$, R$^4$, M, L, x, y and z have the following meaning:

R$^1$, R$^2$, R$^3$ and R$^4$ independently of one another are hydrogen, C$_1$–C$_{20}$-alkyl, C$_1$–C$_{12}$-alkoxy or C$_6$–C$_{10}$-aryl, or R$^1$ and R$^2$ together form a ring having 5 to 30 carbon atoms;

the indices x, y and z having the following meaning:

x is a whole number from 1 to 3, y is a whole number from 1 to 2x+1, y being selected so that the sum of x+z gives a metal oxidation level of +6; the index z is a whole number in the range from 2 to 2x;

M is ruthenium or molybdenum and

L is a donor ligand, with the proviso that, in particular if M is Mo, L is a compound which is derived from a compound of the formula (2), (3) or (4),

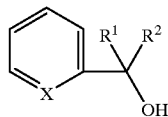

(2)

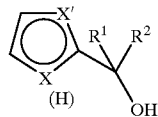

(3)

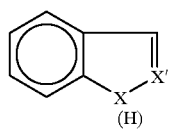

(4)

in which

X is N, O or S and X' is N or C and

R$^1$ and R$^2$ independently of one another are a branched or unbranched, optionally halogenated C$_1$–C$_{12}$-alkyl radical or an optionally substituted C$_6$–C$_{14}$-aryl or heteroaryl radical, or the two together are a group C=O or C=S, or R$^1$ or R$^2$ is a hydrogen radical, and the selectivity in the reaction is ≧40% if a molybdenum compound is used, or the selectivity in the reaction is ≧30% if a ruthenium compound is used.

6. The process as claimed in claim 5, wherein a compound which is derived from 1,1-(C$_1$–C$_6$)-alkyl-1-(2-pyridyl) methanol, 1-(2-pyridyl)-cyclohexan-1-ol, 1-phenyl-1-(2-pyridyl)methanol, 1,1-(C$_1$–C$_6$)-alkyl-1(2thiophenyl) methanol, 1, 1-(C$_1$–C$_6$)-perfluoroalkyl-1-(2-thiophenyl) methanol, 1,1-(C$_1$–C$_6$)-alkyl-1-(2-pyrrolyl)methanol, 1,1-(C$_1$–C$_6$)-alkyl-1-(2-imidazole)methanol, 1,1-(C$_1$–C$_6$)-perfluoroalkyl-1-(2imidazole)methanol is employed as the donor ligand.

7. The process as claimed in claim 5, wherein an aliphatic, optionally branched C$_2$–C$_{30}$-olefin or alicyclic C$_5$–C$_{12}$-olefin is epoxidized.

8. The process as claimed in claim 5, wherein the oxygen used as the oxidizing agent is used in the pure form or is diluted with an inert gas.

9. The process as claimed in claim 5, wherein the reaction temperature is in the range from 30 to 300° C. during the oxidation of C$_6$–C$_{12}$-alkenes and in the range from 120 to 230° C. during the oxidation Of C$_2$–C$_5$-alkenes and the pressure is selected such that the reaction proceeds in the liquid phase.

10. The process as claimed in claim 5, wherein the oxidation is carried out without a solvent, in the pure olefin.

11. The process as claimed in claim 5, wherein the oxidation is carried out in a solvent selected from the group consisting of halogenated aromatics, halogenated or non-halogenated hydrocarbons, C$_1$–C$_{12}$ alcohols or in water.

12. A compound of the formula (1) which readily soluble in organic solvents as a catalyst for selective epoxidization of alkenes $$M_xO_y(L)_z \quad (1)$$

in which the indices x, y and z have the following meaning:

x is a whole number from 1 to 3, y is a whole number from 1 to 2x+1, y being selected so that the sum of x+z gives a metal oxidation number of +6; z is a whole number in the range from 2 to 2x;

M is ruthenium or molybdenum

L is an N, O or S donor ligand, with the proviso that, in particular in the case where M is Mo, L is a compound which is derived from a compound of the formula (2), (3) or (4),

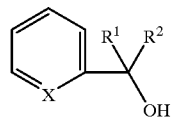

(2)

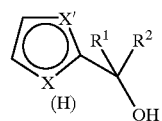

(3)

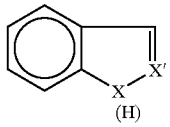

(4)

in which

X is N, O or S and X' is N or C and $R^1$ and $R^2$ independently of one another are a branched or unbranched, optionally halogenated $C_1$–$C_{12}$-alkyl radical or an optionally substituted $C_6$–$C_{14}$-aryl or heteroaryl radical, or the two together are a group C=O or C=S, or $R^1$ or $R^2$ is a hydrogen radical, and the selectivity in the epoxidization reaction is more than 45% if a molybdenum compound is used, and is ≧30% if a ruthenium compound is used.

* * * * *